United States Patent [19]

Uphues et al.

[11] Patent Number: 5,296,622
[45] Date of Patent: Mar. 22, 1994

[54] QUATERNIZED ESTERS

[75] Inventors: Guenter Uphues, Monheim; Uwe Ploog, Haan; Rainer Jeschke, Duesseldorf; Peter Waltenberger, Breitscheid-Hollig, all of Fed. Rep. of Germany

[73] Assignee: Henkel Kommanditgesellschaft auf Aktien, Duesseldorf, Fed. Rep. of Germany

[21] Appl. No.: 949,260

[22] PCT Filed: May 8, 1991

[86] PCT No.: PCT/EP91/00863

§ 371 Date: Nov. 16, 1992

§ 102(e) Date: Nov. 16, 1992

[87] PCT Pub. No.: WO91/17974

PCT Pub. Date: Nov. 28, 1991

[30] Foreign Application Priority Data

May 17, 1990 [DE] Fed. Rep. of Germany ....... 4015849

[51] Int. Cl.$^5$ ................ C07C 219/00; D06M 13/46; C11D 1/62
[52] U.S. Cl. .................................. 554/103; 554/108; 554/110
[58] Field of Search .............. 554/103, 108, 109, 110, 554/113

[56] References Cited

U.S. PATENT DOCUMENTS

| 2,679,462 | 5/1954 | Monson | 106/123 |
| 3,915,867 | 10/1975 | Kang et al. | 252/8.8 |
| 4,767,547 | 8/1988 | Straathof et al. | 252/8.8 |
| 5,068,120 | 11/1991 | Yarger et al. | 534/103 X |
| 5,110,977 | 5/1992 | Wilson et al. | 554/103 X |

FOREIGN PATENT DOCUMENTS

| 0239910 | 10/1987 | European Pat. Off. |
| 0284036 | 8/1988 | European Pat. Off. |
| 1619058 | 12/1967 | Fed. Rep. of Germany |
| 1794068 | 11/1971 | Fed. Rep. of Germany |
| 2430140 | 2/1976 | Fed. Rep. of Germany |
| 3608093 | 9/1987 | Fed. Rep. of Germany |

OTHER PUBLICATIONS

Fette, Seifen und Anstrichmittel, vol. 88, Oct. 1986, M. Münzing et al.: "Kinetik der Fetthärtung und Vergleich verschiedener Katalysatoren", pp. 387–391.

J. Am. Chem. Soc., 79, 4765 (1967), R. L. N. Harris et al.: "Mass Spectrometry in Structural and Sterochemical Problems. CXXXII. Electron Impact Induced Alkyl and Aryl Rearrangements in $\alpha,\beta$-Unsaturated Cyclic Ketones".

DIN 53 924, Nov., 1978.

*Primary Examiner*—Arthur C. Prescott
*Attorney, Agent, or Firm*—Ernest G. Szoke; Wayne C. Jaeschke; Henry E. Millson, Jr.

[57] ABSTRACT

Quaternized esters having fabric-softening and hydrophilicizing properties are obtained by reaction of unsaturated fatty acids containing at least 40 mol-% trans-configured double bonds or esters thereof with alkanolamines and subsequent quaternization of the reaction products with alkylating agents.

19 Claims, No Drawings

QUATERNIZED ESTERS

This invention relates to quaternized esters obtainable by reaction of unsaturated fatty acids—containing at least 40 mol-% trans-configured double bonds—or esters thereof with alkanolamines and subsequent quaternization of the reaction products with alkylating agents and to the use of the products as fabric softeners.

Quaternized esters of saturated fatty acids and alkanolamines are used as fabric softeners (DE-A-16 19 058, DE-A-17 94 68). Particular significance is attributed in this regard to products obtainable by reaction of 2 mol saturated fatty acid with 1 mol triethanolamine and subsequent quaternization with dimethyl sulfate or methyl chloride. Although fabrics treated with quaternized esters of this type show good softness, they often exhibit unwanted hydrophobicity which is reflected in poor wettability or water absorption of the treated fabrics.

There has been no shortage of attempts in the past to solve this problem.

For example, it is known from U.S. Pat. No. 3,915,867 that quaternized esters of mixtures of saturated and unsaturated fatty acids, for example of the type readily obtainable by hydrolysis of natural fats and oils, show good softening power with triethanolamine. It is also disclosed in the patent specification that quaternized esters based on unsaturated fatty acids and alkanolamines have no fabric-softening properties. Accordingly, mixtures of quaternized esters based on saturated and unsaturated fatty acids show poorer performance properties than quaternized esters which have been produced using only saturated fatty acids.

Quaternized triethanolamine triesters based on saturated or monounsaturated fatty acids containing 12 to 22 carbon atoms are known from EP-A-0 239 910. However, products of this type, which have three long fatty acid residues and one short-chain alkyl group, show unsatisfactory softening properties.

Finally, according to the teaching of EP-A 0 284 036, technical mixtures of esters of saturated and unsaturated fatty acids with glycerol, for example of the type obtainable from natural fats and oils, can be transesterified with alkanolamines and then quaternized. Since quaternized esters of this type in turn contain unsaturated components, they are inferior to saturated products in terms of softness.

Accordingly, the problem addressed by the present invention was to provide quaternized esters of fatty acids with alkanolamines which would be capable both of providing fabrics with good softness and of imparting a high degree of hydrophilicity.

The present invention relates to quaternized esters obtainable by

A) reaction of monounsaturated $C_{16-22}$ fatty acids containing at least 40 mol-% trans-configured double bonds or esters thereof with glycerol or aliphatic $C_{1-4}$ alcohols with alkanolamines corresponding to formula (I)

in which $R^1$ and $R^2$ are independently of one another $C_{2-4}$ hydroxyalkyl groups and $R^3$ is either a $C_{2-4}$ hydroxyalkyl group or a $C_{1-22}$ straight or branched alkyl group, and B) subsequent quaternization of the reaction products with alkylating agents.

The invention is based on the observation that quaternized esters of fatty acids containing at least 40 mol-% trans-configured double bonds with alkanolamines provide textiles with surprisingly good softness during the softening treatment and, in addition, have a less hydrophobicizing effect.

Suitable fatty acids for the preparation of the quaternized esters according to the invention are, in particular, elaidic acid and technical fatty acid fractions rich in elaidic acid which contain at least 40 mol-% fatty acids having trans-configured double bonds.

Other suitable starting materials for the production of the quaternized esters are esters of the above-mentioned fatty acids with alcohols containing 1 to 4 carbon atoms. Typical examples are ethyl, n-propyl, i-propyl, n-butyl or, more particularly, methyl esters. In addition, in one particular embodiment of the invention, the fatty acids may be present as full or partial esters of glycerol.

Unsaturated fatty acids containing at least 40 mol-% trans-configured double bonds or esters thereof may be prepared from linoleic acid or esters thereof which are selectively hydrogenated in the presence of modified nickel catalysts to form mixtures of monounsaturated fatty acids of high elaidic acid content ("trans content") or esters thereof. Another possibility is to isomerize cis-octadecenoic acid (oleic acid) or esters thereof in the presence of selenium or nitric acid to form trans-octadecenoic acid (elaidic acid) or esters thereof. Processes such as these for the preparation of elaidic acid and elaidic acid esters have long been known and are described, for example, in Fette, Seifen, Anstrichmittel, 88, 387 (1987) or J. Am. Chem. Soc., 79, 4765 (1967).

As usual in oleochemistry, technical mixtures of fatty acids or esters thereof obtained from natural fats and oils may also be used for the production of the unsaturated fatty acids containing at least 40 mol-% trans-configured double bonds or esters thereof. In this case, the trans content of the saturated components present in the technical mixtures is limited. Accordingly, it is preferred to start out from products which have a high content of linoleic or oleic acid and a low content of saturated compounds, such as for example sunflower oil or rapeseed oil.

Quaternized esters having particularly good performance properties are obtained by reaction of technical elaidic acid mixtures containing at least 40 mol-%, preferably at least 50 mol-% and more preferably more than 60 mol-% elaidic acid with alkanolamines corresponding to formula (I) and subsequent quaternization of the reaction products with alkylating agents.

Suitable alkanolamines are di- and trialkanolamines and mixtures thereof. Typical examples are methyl diethanolamine, ethyl diethanolamine, coconut alkyl diethanolamine, methyl diisopropanolamine or triethanolamine.

Quaternized esters having particularly good performance properties are obtained by reaction of the unsaturated fatty acids with alkanolamines corresponding to formula (I), in which $R^1$, $R^2$ and $R^3$ represent a hydroxyethyl group, and subsequent quaternization of the reaction products with alkylating agents.

The present invention also relates to a process for the production of quaternized esters in which unsaturated $C_{16-22}$ fatty acids containing at least 40 mol-% trans-configured double bonds or esters thereof with glycerol or aliphatic $C_{1-4}$ alcohols are reacted with alkanolamines corresponding to formula (I),

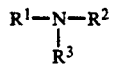

in which $R^1$ and $R^2$ are independently of one another $C_{2-4}$ hydroxyalkyl groups and $R^3$ is either a $C_{2-4}$ hydroxyalkyl group or a $C_{1-22}$ straight or branched alkyl group, and B) the reaction products are subsequently quaternized with alkylating agents.

Where free fatty acids are introduced into the reaction, an esterification takes place with the alkanolamines. The reactants may be used in a molar ratio of fatty acid to alkanolamine of from 1.2:1 to 2.5:1. Quaternized esters having particularly good performance properties contain on average two ester groups. It is therefore of advantage to carry out the reaction with a molar starting ratio of 1.5 to 2.5 and, more particularly, 1.9 to 2.2.

If esters of unsaturated fatty acids are used, a transesterification takes place with the alkanolamines. The conditions mentioned above apply to the quantities in which the reactants are used. In the transesterification of di- or triglycerides with alkanolamines, the molar quantities used are based on the molar quantity of the fatty acid residues present in the fatty acid glycerol esters.

The esterification of the fatty acids with the alkanolamines may be carried out at a temperature of 150° to 220° C. An optimal reaction velocity is reached if the reaction is carried out at a temperature in the range from 180° to 200° C. The reaction is continued until the reaction product has an acid value below 5.

The transesterification of the fatty acid esters with the alkanolamines may be carried out at lower temperatures of 80° to 220° C. and preferably 80° to 150° C. in the presence of 0.1 to 0.5% by weight of a basic catalyst, for example sodium methylate. If desired, the alcohol formed during the reaction may be removed by distillation before quaternization of the esters.

After the esterification or transesterification, the crude product is reacted with alkylating agents, more particularly with $C_{1-3}$ straight or branched chain alkyl or $C_{7-10}$ aralkyl halides, phosphates or sulfates, for example methyl chloride, benzyl chloride, trimethyl phosphate or preferably dimethyl sulfate. The quaternization may be carried out in bulk or in solvents, for example water or lower alcohols, at temperatures in the range from 60° to 120° C. and preferably at temperatures in the range from 80° to 100° C. To ensure that the quaternization product is free from unreacted alkylating agent, 0.7 to 1.0 mol alkylating agent is used per mol ester.

Particularly good performance properties are shown by quaternized esters in which the quaternary nitrogen atom has two long-chain substituents and two short-chain substituents, for example compounds obtained by esterification of triethanolamine or methyl diethanolamine with, on average, 2 mol unsaturated fatty acid and subsequent quaternization with dimethyl sulfate.

In the softening treatment of yarns, woven fabrics or knitted goods, the quaternized esters provide the fabrics with good softness and a high degree of hydrophilicity. Accordingly, they are suitable as fabric softeners and for the production of fabric and textile softeners.

The following Examples are intended to illustrate the invention without limiting it in any way.

EXAMPLES

I Technical Fatty Acids Used

Fatty acid A was obtained by selective hydrogenation of technical sunflower oil fatty acid containing 62% by weight linoleic acid in the presence of modified nickel catalysts using the method described in Fette, Seifen, Anstrichmittel, 88, 387 (1987). After selective hydrogenation, fatty acid A had a trans content of 62% by weight. To produce fatty acids B to E having trans contents of 50 to 31% by weight, fatty acid A was mixed with technical oleic acid or stearic acid. The characteristic data of the fatty acids used are shown in Table 1.

TABLE 1

| | Technical Fatty Acids | | |
|---|---|---|---|
| Fatty acid | Acid value | Iodine value | Trans content % by weight |
| A | 197.7 | 89.5 | 62 |
| B | 199.5 | 72.3 | 50 |
| C | 198.2 | 90.2 | 50 |
| D | 199.0 | 91.2 | 31 |
| E | 202.5 | 45.5 | 32 |

The products based on technical fatty acids having a trans content of at least 40 mol-% (A–C) correspond to the invention; products based on technical fatty acids of lower trans content (D, E) are comparison products.

II. Production Examples

Example 1

General Procedure for the Condensation of Fatty Acids With Triethanolamine 426 g (1.5 mol) fatty acid A were introduced into a 1 liter three-necked flask equipped with a stirrer, internal thermometer and reflux condenser and, after heating to 80° C., 111.8 g (0.75 mol) triethanolamine were added. The reaction mixture was heated to 200° C. over a period of 4 h and stirred for 1 h at that temperature, 27 g water of reaction being separated. 509 g of a yellow liquid having an acid value of 4.7 and containing 2.0% by weight titratable nitrogen were obtained after cooling to 20° C.

250 g of the reaction product were transferred to a 500 ml four-necked flask equipped with a stirrer, internal thermometer, dropping funnel and reflux condenser and quaternized with 37.9 g dimethyl sulfate for 1.5 h at 80 to 85° C. The reaction mixture was then stirred for 1 h at 85° C. 387 g of a semisolid product obtained, its degree of quaternization—as determined by subtraction after two-phase titration in acidic and alkaline medium—being 84% by weight. 80 g of the quaternized product and 320 g water were stirred for 30 minutes at 80° C. to form a finely divided dispersion and then cooled to 20° C. (product A*).

Examples 2 and 3, Comparison Examples 1 and 2

Example 1 was repeated using technical fatty acid of high trans content (fatty acids B and C, Examples 2 and 3) or low trans content (fatty acids D and E, Comparison Examples 1 and 2). Products B* to E* were obtained.

III Application Examples

Cotton fabric (molleton) which had become hard through repeated washing was treated by padding with the products of Examples 1 to 3 and Comparison Examples 1 and 2. The treatment was carried out under the following conditions:

Concentration: 30 g/l of the 20% by weight products
Liquor uptake: approx. 80% by weight, based on dry fabric
Drying: 3 mins. at 180° C.

The treated test fabrics were evaluated for rewettability and softness. Rewettability was determined by the rise level test according to DIN 53 924 in which the level to which water rises in mm was evaluated after 1 minute. Softness was evaluated subjectively by six experienced people who could award marks on a scale from 0=hard and rough to 6=soft and voluminous. The test results are set out in Table 2.

Cotton terry was treated under the same conditions. Evaluation of softness produced results comparable with the molleton.

TABLE 2

| | Rewettability and Softness | |
|---|---|---|
| Example | Fatty acid | Rise level mm | Feel mark |
| 1 | A* | 10 | 5.5 |
| 2 | B* | 5 | 5.5 |
| 3 | C* | 12 | 5.0 |
| C1 | E* | 0 | 5.5 |
| C2 | F* | 15 | 4.5 |

We claim:

1. An ester quaternized with an alkylating agent wherein the ester is the reaction product of a) a monounsaturated $C_{16-22}$ fatty acid or mixture of such fatty acids or an ester of the foregoing with glycerol or an aliphatic $C_{1-4}$ alcohol wherein the fatty acid moieties contain at least 40 mol % trans-configuration double bonds, and b) an alkanolamine of formula I

in which $R^1$ and $R^2$ are independently $C_{2-4}$ hydroxyalkyl groups and $R^3$ is either a $C_{2-4}$ hydroxyalkyl group or a $C_{1-22}$ straight or branched alkyl group.

2. The quaternized ester of claim 1 in which the ester is the reaction product of technical elaidic acid or an ester thereof with an alkanolamine of formula I.

3. The quaternized ester of claim 1 wherein in the alkanolamine of formula I, $R^1$, $R^2$ and $R^3$ are all hydroxyethyl groups.

4. The quaternized ester of claim 1 wherein the alkylating group is a straight or branched chain $C_{1-3}$ alkyl group or a $C_{7-10}$ aralkyl group.

5. The quaternized ester of claim 1 wherein the molar ratio of component a) to component b) is from about 1.2:1 to about 2.5:1.

6. The quaternized ester of claim 5 wherein said molar ratio is from about 1.5:1 to about 2.5:1.

7. The quaternized ester of claim 5 wherein said molar ratio is from about 1.9 to about 2.2.

8. The quaternized ester of claim 1 wherein the alkanolamine of formula I is triethanolamine or methyl diethanolamine and the alkylating group is methyl.

9. A process for the preparation of a quaternized ester product comprising the steps of
A) reacting a) a monounsaturated $C_{16-22}$ fatty acid or a mixture of such fatty acids or an ester of the foregoing with glycerol or an aliphatic $C_{1-4}$ alcohol wherein the fatty acid moieties contain at least 40 mol % trans-configuration double bonds, with b) an alkanolamine of formula I

in which $R^1$ and $R^2$ are independently $C_{2-4}$ hydroxyalkyl groups and $R^3$ is either a $C_{2-4}$ hydroxyalkyl group or a $C_{1-22}$ straight or branched alkyl group; and B) reacting the product from step A) with an alkylating agent to produce the quaternized ester product.

10. The process of claim 9 in which in step A) technical elaidic acid is used as component a).

11. The process of claim 9 wherein in the alkanolamine of formula I, $R^1$, $R^2$ and $R^3$ are all hydroxyethyl groups.

12. The process of claim 9 wherein in step B) the alkylating group is a straight or branched chain $C_{1-3}$ alkyl group or a $C_{7-10}$ aralkyl group.

13. The process of claim 9 wherein in step A) the molar ratio of component a) to component b) is from about 1.2:1 to about 2.5:1.

14. The process of claim 13 wherein said molar ratio is from about 1.5:1 to about 2.5:1.

15. The process of claim 13 wherein said molar ratio is from about 1.9 to about 2.2.

16. The process of claim 9 wherein in step A) the alkanolamine of formula I is triethanolamine or methyl diethanolamine and in step B) the alkylating group is methyl.

17. In a process for softening textiles, the improvement wherein a textile softening quantity of the quaternized ester of claim 1 is used in the process.

18. In a process for softening textiles, the improvement wherein a textile softening quantity of the quaternized ester of claim 4 is used in the process.

19. In a process for softening textiles, the improvement wherein a textile softening quantity of the quaternized ester of claim 8 is used in the process.

* * * * *